US00PP20375P3

(12) United States Plant Patent
Maloy

(10) Patent No.: US PP20,375 P3
(45) Date of Patent: Oct. 6, 2009

(54) *VRIESEA* PLANT NAMED 'KIWI DUSK'

(50) Latin Name: *Vriesea lindl*
Varietal Denomination: Kiwi Dusk

(76) Inventor: Andrew Maloy, 16 Riverlea Road, Whenupai, Waitakere (NZ), 1000

( * ) Notice: Subject to any disclaimer, the term of this patent is extended or adjusted under 35 U.S.C. 154(b) by 0 days.

(21) Appl. No.: 11/978,481

(22) Filed: Oct. 29, 2007

(65) Prior Publication Data

US 2009/0113583 P1 Apr. 30, 2009

(51) Int. Cl.
*A01H 5/00* (2006.01)

(52) U.S. Cl. ..... Plt./370

(58) Field of Classification Search ..... Plt./370
See application file for complete search history.

(56) References Cited

PUBLICATIONS

GTITM UPOVROM Citation for 'Kiwi Dusk'as Per NZ PBR BRO003; Oct. 5, 2005.*

* cited by examiner

*Primary Examiner*—Kent L Bell

(57) ABSTRACT

A new and distinct *Vriesea* cultivar named 'Kiwi Dusk' is disclosed, characterized by very stable, strongly reticulate variegated foliage of dark green/bronze/dark purple. Upright plant form with a dark purple heart.

1 Drawing Sheet

Figure 1:
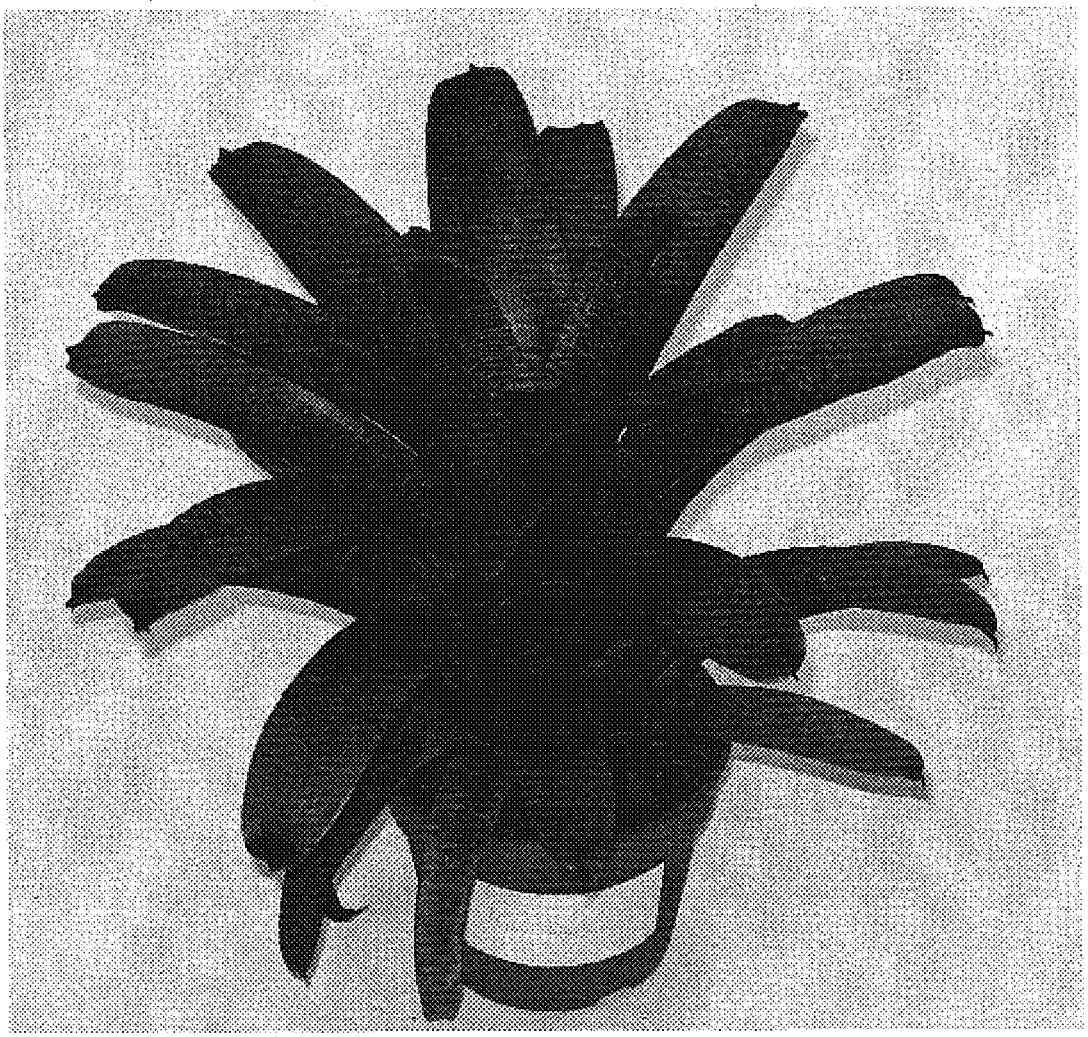

Latin name of the genus and species: *Vriesea lindl.*
Variety denomination: 'KIWI DUSK'.

BACKGROUND OF THE INVENTION

The new cultivar is a product of a planned breeding program. The new variety originated from a cross pollination of an unnamed, seed parent and an unnamed, pollen parent, both *Vriesea fosteriana* made by the inventor during 1996.

It was discovered by the inventor, Andrew Maloy, a citizen of New Zealand, in 1999 in a group of seedlings resulting from the 1996 crossing.

Asexual reproduction of the new cultivar 'Kiwi Dusk' was first performed in Auckland, New Zealand, in a commercial laboratory by tissue culture in 2002. 'Kiwi Dusk' has been reproduced by micro-propagation and has shown that the unique features of this cultivar are stable and reproduced true to type.

SUMMARY OF THE INVENTION

The cultivar 'Kiwi Dusk' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Kiwi Dusk.' These characteristics in combination distinguish 'Kiwi Dusk' as a new and distinct *Vriesea* cultivar:

1. Foliage resistant to stress.
2. Foliage is dark green and bronze/dark purple with distinct transverse markings.
3. Paler coloring at base of leaves.
4. Suitability as an indoor pot plant.
5. Broad leaves occurring in right, regular whorls.

Plants of the new cultivar 'Kiwi Dusk' cannot be compared to either seed parent or pollen parent as records of those characteristics were not kept. However, 'Kiwi Dusk' can be compared to the commercial variety *Vriesea fosteriana* 'Red Chestnut.' Plants of 'Red Chestnut' are similar to plants of 'Kiwi Dusk' in most horticultural characteristics, however, 'Red Chestnut 'has a plain, uncolored heart and lighter green leaves than 'Kiwi Dusk.'

'Kiwi Dusk' can also be compared to it seedling siblings, 'Kiwi Cream', filed concurrently and assigned Ser. No. 11/978,481 and 'Kiwi Sunset' filed concurrently and assigned Ser. No. 11/978.480. 'Kiwi Dusk' differs from 'Kiwi Cream' in having overall much darker foliage and a darker center to the plant. 'Kiwi Dusk' is also normally shorter than 'Kiwi Cream.' 'Kiwi Dusk' differs from 'Kiwi Sunset' in having darker foliage and a center to the plant with more dark purple, rather than pink tones.

BRIEF DESCRIPTION OF THE PHOTOGRAPH

The accompanying photograph in FIG. 1 illustrates in full color a typical plant of 'Kiwi Dusk' grown in a greenhouse. This plant is approximately 4 years, 6 months old, shown in a 17 cm pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'Kiwi Dusk' plants grown in a climate controlled greenhouse in Saint Oedenrode, the Netherlands. Temperatures ranged from 18° C. to 22° C. at night to 18° C. to 22° C. during the day. No artificial light, photoperiodic treatments or chemical treatments were given to the plants. Measurements and numerical values represent averages of typical plant types.

Botanical classification: *Vriesea fosteriana* cultivar 'Kiwi Dusk.'

PROPAGATION

Time to rooting: 2 months, from a 2 year old tissue culture at approximately 20 to 22° C.
Root description: Fine, fibrous. Free Branching

PLANT

Growth habit: Upright, forming compact rosettes around a single axis.
Plant shape: Inverted triangle.
Height: Approximately 28.2 cm.
Plant spread: Approximately 44.5 cm.
Normal pot size: 15 cm and larger.
Growth rate: Slow.
Branching characteristics: Upright, non-branching.
Number of leaves per stem: Approximately 28.
Age of plant described: Approximately 4 years, 6 months.

FOLIAGE

Leaf:
*Arrangement.*—Whorled.
*Average length.*—Approximately 28.2 cm.
*Average width.*—Approximately 6.8 cm.
*Shape of blade.*—Oblong.
*Aspect.*—Slightly recurved.
*Apex.*—Sharply acute
*Base.*—Decurrent
*Margin.*—Entire.
*Texture of top surface.*—Smooth, moderately glossy.
*Texture of bottom surface.*—Smooth, moderately glossy.
*Color.*—
*Young foliage upper side.*—Near R.H.S. Yellow-green 145A and Yellow-green 145B, individually present with a greyed-purple reticulate variegation of N186C/N187A, individually present lighter towards the base of the leaf. Tip greyed-purple N186C.
*Young foliage under side.*—Near R.H.S. Greyed-red; 182B, darker towards the tip; 182A. Outer tip greyed-purple N186A Leaf blade has a greyed-red to greyed-purple reticulate variegation; 178A and 178B, individually present to to 183A and 183B, individually present variegation color is lighter towards the base of the leaf. Base is yellow-green 145C.
*Mature foliage upper side.*—Near R.H.S. Green; 137A and 137B, individually present. Base greyed-green; 192A and 192B, present individually. Outer base greyed-orange; 166A. Upper leaf blade with a green to yellow-green reticulate variegation; Darker than 139A. Overall upper leaf surface has a grayish hue. Tip greyed-purple; 187A.
*Mature foliage under side.*—Near R.H.S. Yellow-green, 145A, darker towards the tip, close to 146A, lighter towards the base; 145C. Outer tip greyed-purple 187A. Leaf blade with a greyed-purple reticulate variegation N186A, flushed yellow-green 146A towards the top.
Venation:
*Type.*—Parallel.
*Venation coloration.*—Identical/Indistinguishable from foliage.
Petiole: Not present, sessile.

FLOWER

Flowering has not been observed, and is not commercially important in this cultivar.

OTHER CHARACTERISTICS

Disease and pest resistance: Neither resistance nor susceptibility to diseases or usual pests of *Vriesea,* such as scale acid mealy bug, has been observed in this variety.
Drought tolerance and cold tolerance: Observed to tolerate temperatures to 35° C. without any negative effects. Temperature tolerance above this range has not been observed. Tolerance of cold temperatures have not been observed.
Fruit/Seed production: Not observed.

What is claimed is:

1. A new and distinct cultivar of *Vriesea* plant named 'Kiwi Dusk' as herein illustrated and described.

* * * * *